(12) United States Patent
Yang et al.

(10) Patent No.: US 6,679,880 B2
(45) Date of Patent: Jan. 20, 2004

(54) ELECTROSURGICAL HAND PIECE

(75) Inventors: Liang-Pang Yang, Chang Hua (TW); Hsueh-Cheng Liao, Chang Hua (TW)

(73) Assignee: Par Value International Limited, Nan Tou Hsien (TW)

( * ) Notice: Subject to any disclaimer, the term of this patent is extended or adjusted under 35 U.S.C. 154(b) by 0 days.

(21) Appl. No.: 09/910,026

(22) Filed: Jul. 23, 2001

(65) Prior Publication Data

US 2003/0018328 A1 Jan. 23, 2003

(51) Int. Cl.[7] ................................................ A61B 18/18
(52) U.S. Cl. ........................................... 606/41; 606/49
(58) Field of Search ............................. 606/41, 42, 43, 606/44, 45, 46, 47, 48, 49, 50

(56) References Cited

U.S. PATENT DOCUMENTS

| | | | | |
|---|---|---|---|---|
| 4,040,426 A | * | 8/1977 | Morrison, Jr. | 219/121.36 |
| 4,781,175 A | * | 11/1988 | McGreevy et al. | 219/121.5 |
| 5,098,430 A | * | 3/1992 | Fleenor | 606/42 |
| 5,217,457 A | * | 6/1993 | Delahuerga et al. | 606/37 |
| 5,256,138 A | * | 10/1993 | Burek et al. | 606/42 |
| 5,320,621 A | * | 6/1994 | Gordon et al. | 600/372 |
| RE34,780 E | * | 11/1994 | Trenconsky et al. | 219/121.5 |
| 5,449,356 A | * | 9/1995 | Walbrink et al. | 606/37 |
| 5,827,280 A | * | 10/1998 | Sandock et al. | 606/46 |
| 6,013,075 A | * | 1/2000 | Avramenko et al. | 219/121.48 |

* cited by examiner

Primary Examiner—Michael Peffley
(74) Attorney, Agent, or Firm—Browdy and Neimark, P.L.L.C.

(57) ABSTRACT

An electrosurgical hand piece comprises a handle having therein a handle passageway. A grip sleeve is provided on handle. A nozzle is disposed at one end of the handle. The outer side of the nozzle has a contacting portion. The nozzle has a nozzle passageway in communication with the handle passageway of the handle. The rear end of the nozzle has a first support portion. A support member is disposed in the nozzle passageway of the nozzle to form the second support portion of the nozzle. An electrode is fixed at the rear side by the first support portion of the nozzle to enable the electrode to extend into the nozzle passageway and supported at the front side thereof by the support member. So that, the electrode is supported by both the first support portion and the support member. Whereby the electrode is kept along the central line of the nozzle passageway of the nozzle to provide the surgeon can operate the hand piece precisely in the surgical operation. The surgeon can move aside the healthy tissue by the contacting portion for facilitating the surgical operation, and the grip sleeve will prevent the surgeon from fatigue in a long time surgical operation.

14 Claims, 3 Drawing Sheets

ELECTROSURGICAL HAND PIECE

FIELD OF THE INVENTION

The present invention relates generally to a surgical device, and more particularly to an electrosurgical hand piece.

BACKGROUND OF THE INVENTION

The U.S. Pat. No. 4,901,719 discloses an electrosurgical hand piece comprising a handle, a nozzle, and an electrode. The nozzle is disposed at the front end of the handle and is provided with a nozzle passageway. The nozzle is provided at the rear end with a trailing body which is in turn provided with a receiving hole, in which the electrode is fixed such that the front end of the electrode is received in the nozzle passageway. The handle is connected at the rear end with a gas delivery apparatus by a tube. The gas, which generally is argon, is emitted by the nozzle via the handle passageway of the handle for removing the body fluid in the vicinity of a tissue under treatment. The electrode is connected with an electrosurgical generator (ESG) by a bonding wire via which the electrical energy provided by the ESG is transferred to the electrode. The electrode is thus made to generate a high voltage discharge for creating about an electrosurgical effect on a target tissue.

Such a prior art electrosurgical hand piece as described above is defective in design in that the electrode has only one supporting point such that the front end of the electrode is suspended, and that the electrode is apt to move aside in the surgical operation. As a result, a surgeon often fails to control with precision the action point of the electrosurgical effect provided by the electrosurgical hand piece. In addition, the head of the nozzle of the prior art electrosurgical hand piece is so fastigiated that it can not be used by a surgeon as a means to push away the healthy tissue to facilitate the treatment of the diseased or deformed tissue.

SUMMARY OF THE INVENTION

It is the primary objective of the present invention to provide an electrosurgical hand piece comprising a nozzle and an electrode which is securely received in place by the nozzle to prevent the electrode from swaying or tilting.

It is another objective of the present invention to provide an electrosurgical hand piece which enables a surgeon to use the hand piece to push away the tissue so as to facilitate the surgery of a specific tissue under treatment.

In keeping with the principle of the present invention, the foregoing objectives of the present invention are attained by an electrosurgical hand piece comprising a handle with a handle passageway. A nozzle is disposed at one end of the handle and is provided with a nozzle paggageway in communication with the handle passageway. The nozzle is provided at the rear end with a first support portion, and in the nozzle passageway thereof with a second support portion. An electrode is fastened at the rear end thereof with the first support portion such that the front end of the electrode is supported by the second support portion. In light of the electrode being supported by two supporting points, the electrode is prevented from deviating from the center line of the nozzle passageway in the course of a surgical operation.

DETAILED DESCRIPTION OF THE INVENTION

Figure 1:
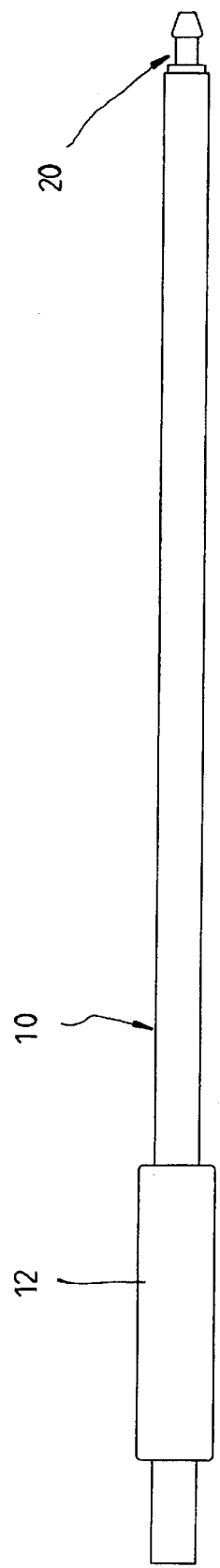
FIG. 1 shows a perspective view of a preferred embodiment of the present invention.

As shown in all drawings provided herewith, an electrosurgial hand piece embodied in the present invention comprises the following component parts.

A handle 10 is of a long tubular construction and is provided in the interior with a handle passageway 11. The handle 10 is connected at the rear end with one end of a tube 50 which is in turn connected at other end thereof with a gas delivery device 60 serving to provide the electrosurgical hand piece of the present invention with a predetermined gas, such as argon, via the tube 50. The handle passageway 11 of the handle 10 is provided therein with a bonding wire 71, which is connected with an electrosurgical generator 70.

A grip sleeve 12, which is a tube made of soft material, such as soft rubber or foaming material is provided on the handle 10 in interference fit status, but permits a user to shift the grip sleeve 12 along the handle 10 to locate at the position as he/she wants. A surgeon can grip the grip sleeve 12 to operate the hand piece of the present invention. The grip sleeve 12 provides the surgeon with an improved grip preventing fatigue during a long surgical operation.

Figure 2:
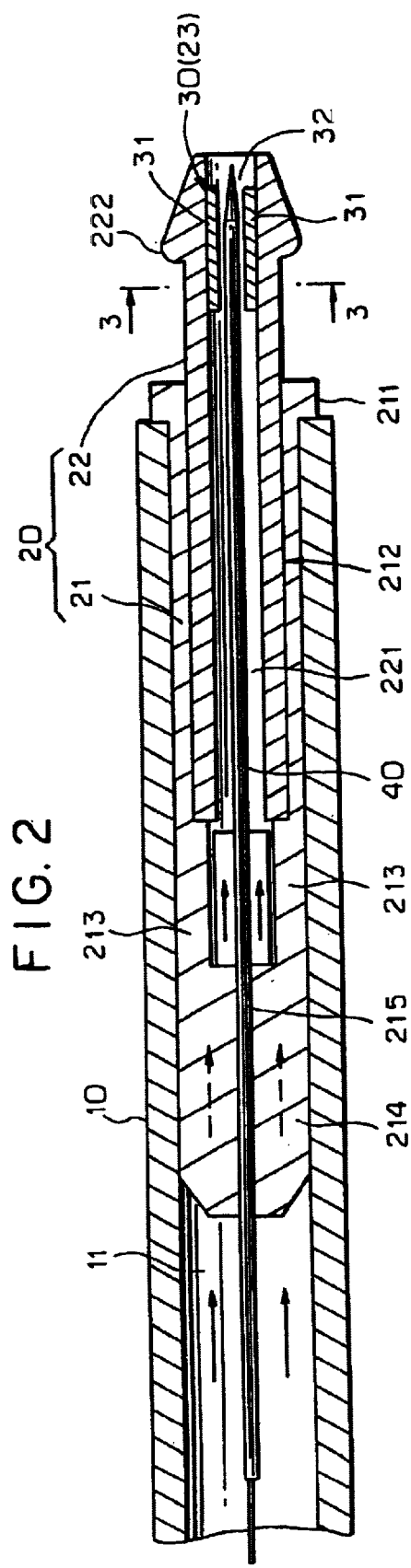
FIG. 2 shows a partial longitudinal sectional view of the structure of the preferred embodiment of the present invention.
Figure 3:
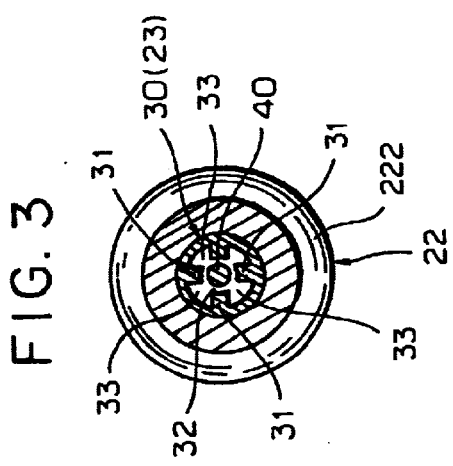
FIG. 3 shows a sectional view taken along the direction indicated by a line 3—3 as shown in FIG. 2.

A nozzle 20 has a base 21 and a head 22. The base 21 is provided at the front end with a stop portion 211, and in the center with a receiving hole 212. The base 21 is provided at the rear end with two extension arms 213 extending therefrom. The two extension arms (213) having at the outer ends thereof a first support portion 214 and at the center thereof a receiving hole 215. The support portion 214 permitting passages of gas along its side as shown in FIG. 2. The one end of the base 21, where the first support portion 214 is located, is snugly received in the handle 10 such that the stop portion 211 is rested against the handle 10. The head 22 is provided with a nozzle passageway 221 and a contacting portion 222 located at the outer side in proximity of the front end thereof. The contacting portion 222 is greater in outer diameter than the rest portion of the head 22 such that the front end of the outer diameter facing the head 22 becomes progressively smaller. The rear end of the head 22 is snugly received in the receiving hole 212 of the base 21, thereby enabling the gas to be emitted from the nozzle passageway 221 of the head 22 of the nozzle 20 via the tube 50 and the handle passageway 11.

A support member 30 is made of an insulation material, such as a semiconductor or ceramic. The support member 30 is a tubular body and is provided in the interior with four ribs 31 radially such that a opening 32 is formed between the top ends of the ribs 31, and that four channels 33 are formed between the adjoining ribs 31. The support member 30 is snugly disposed in the nozzle passageway 221 of the head 22 of the nozzle 20 and is located in proximity of a predetermined position of the front end opening of the nozzle passageway 221, thereby resulting in formation of the second support portion 23 of the nozzle 20.

The support member 30 of the preferred embodiment of the present invention is an independent element. In practice, the circular wall of the nozzle passageway 221 may be provided with two or more ribs 31 which are formed integrally, thereby resulting in formation of the second support portion 23 in the nozzle 20.

An electrode 40 has a pointed front end. The electrode 40 is fixed at one side in proximity of the rear end thereof in the receiving hole 215 of the first support portion 214 of the nozzle base 21. One side in proximity of the front end of the electrode 40 is put through the opening 32 of the support member 30 in a loose-fitting manner. In other words, the outer ends of the ribs 31 may be slightly in contact with the electrode 40 or the outer ends of the ribs 31 may be separated from the electrode 40 by a minute interstice for supporting the electrode 40. The electrode 40 is thus supported simultaneously by the first support portion 214 and the support member 30 (the second support portion 23) such that the electrode 40 is kept at a predetermined position, and that the electrode 40 is prevented from moving aside. The electrode 40 is connected at the rear end with the bonding wire 71 via which the electrical energy generated by the electrosurgical generator 70 is transmitted to the electrode 40.

Figure 4:
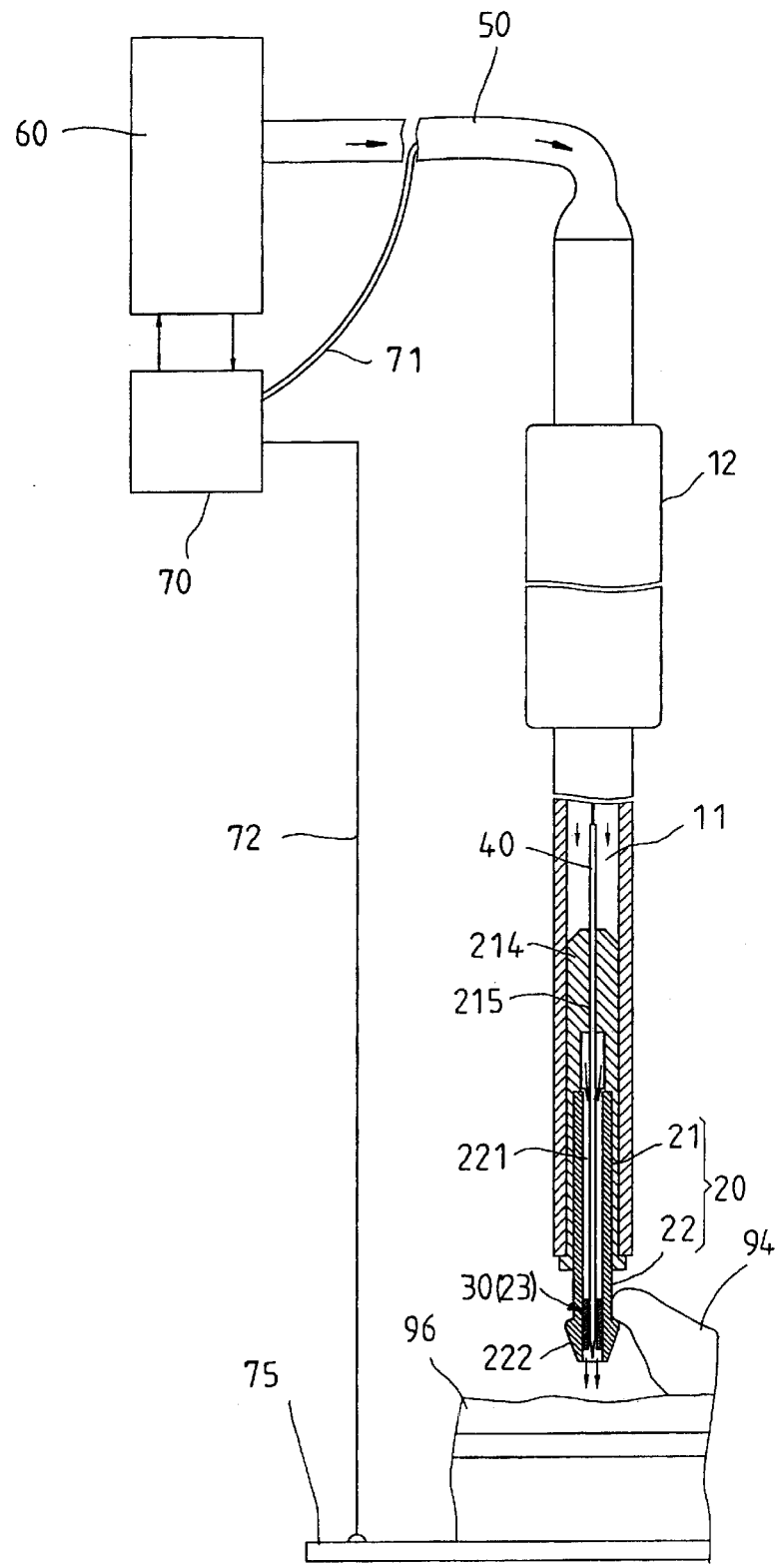
FIG. 4 shows a schematic view of the preferred embodiment of the present invention in use.

As illustrated in FIG. 4, the use of the present invention a first step in which a ground wire 72 of the electrosurgical generator 70 is connected with a conductive plate 75 on which a patient lies. An attendant surgeon holds the handle 10 to enable the contacting portion 222 of the nozzle 20 to push away a healthy tissue 94 so as to orient at a target tissue 96. Subsequently, the gas delivery device 60 is started to enable the gas to flow through the nozzle passageway 221 of the nozzle 20 via the tube 50 and the handle passageway 11, and then through the channel 33 of the support member 30 before being emitted from the front end opening of the nozzle passageway 221 (as the arrows show in FIGS. 2 and 4) for removing the body fluid in the vicinity of the target tissue 96. The electrosurgical generator 70 is started at the same time such that the current is transmitted to the electrode 40 via the bonding wire 71. As a result, a high voltage discharge is brought about by the electrode 40 for treating the target tissue 96. In light of the electrode 40 being supported by the first support portion 214 and the support member 30 (the second support portion 23), the electrode 40 is secured in place along the center line of the nozzle passageway 221 in the course of the surgical operation, thereby enabling the attendant surgeon to control precisely the position of the electrosurgical effect on the target tissue 96 so as to improve the efficiency of the surgical operation.

The contacting portion 222 of the nozzle 20 is to facilitate the moving of the healthy tissue by the surgeon in the course of surgery. The contacting portion 222 may be embodied in other forms. For example, the contacting portion may be formed of a plurality of protruded rings which are arranged in a parallel manner. In addition, the contacting portion 222 may be formed of a protruded ring of a spiral shape. In other words, the embodiment described above is to be regarded in all respects as being merely illustrative and not restrictive. The present invention is therefore to be limited only by the scopes of the following claims.

The advantages of the present invention are: first, the electrode 40 is supported by both the first support portion 214 and the support member 30 (the second support portion 23), so that the electrode 40 is kept along the central line of the nozzle passageway 221 of the nozzle 20 to provide the surgeon can operate the hand piece of the present invention precisely in the surgical operation. Second, the surgeon can move aside the healthy tissue by the contacting portion 222 of the nozzle 20 for facilitating the surgical operation, and the grip sleeve 12 will prevent surgeon from fatigue in a long time surgical operation.

What is claimed is:

1. An electrosurgical hand piece comprising:
   a handle provided in an interior with a handle passageway in communication with a tube for allowing a predetermined gas to pass therethrough;
   a nozzle disposed at one end of said handle and provided with a nozzle passageway in communication with said handle passageway of said handle to enable emission of the gas from said nozzle passageway; a first support portion having a receiving hole and being fixed on an inner wall of said handle passageway behind said nozzle; the first support portion permitting passage of the gas there around into said nozzle passageway;
   an electrode fixed at a rear end thereof in said receiving hole of said first support portion to enable said electrode to extend into said nozzle passageway, said electrode capable of receiving electrical energy via a bonding wire to bring about a high voltage discharge; and
   said nozzle passageway provided therein with a second support portion having at least one channel for passage of the gas, and a passage for said electrode to pass therethrough.

2. The electrosurgical hand piece as defined in claim 1, wherein said nozzle is provided on an outer surface with a contacting portion for use in moving away a healthy tissue obstructing a diseased or deformed tissue under treatment;
   wherein said contacting portion is an annular projection with an outer diameter greater than that of the nozzle, the projection having a rear side spaced apart from a corresponding end of the handle and a front side which is inclined to the outlet of the nozzle.

3. The electrosurgical hand piece as defined in claim 1, further comprising a grip on the handle for gripping the hand piece by a user, the grip being adjustable on the handle.

4. The electrosurgical hand piece as defined in claim 1, wherein said second support portion of said nozzle is engaged to a tubular wall of said nozzle passageway and is radially provided with a plurality of ribs such that said channel is formed between two adjoining ribs, and that said passage is formed between free ends of said ribs.

5. The electrosurgical hand piece as defined in claim 1 wherein said second support portion is formed by a support member provided in said nozzle passageway of said nozzle; said support member being a tubular construction and provided in an interior with a plurality of ribs extending radially such that said channel is formed between two adjoining ribs, and that said passage is formed between free ends of said ribs.

6. The electrosurgical hand piece as defined in claim 1, wherein said nozzle comprises a base and a head engaged to the base, said base being provided at a rear end with said first support portion, and at a front end with a receiving hole, said head being provided with said nozzle passageway, said head being fixed at one end thereof in said receiving hole of said base, said base being fixed in said handle.

7. The electrosurgical hand piece as defined in claim 1, further comprising a contacting portion formed by at least one protruded ring on a front end of said nozzle spaced apart from a corresponding end of the handle.

8. An electrosurgical hand piece comprising:
   a handle provided in an interior with a handle passageway in communication with a tube for allowing a predetermined gas to pass therethrough;
   a nozzle disposed at one end of said handle and provided with a nozzle passageway in communication with said handle passageway of said handle to enable emission of the gas from said nozzle passageway; a first support portion having a receiving hole and being fixed on an inner wall of said handle passageway behind said nozzle; the first support portion permitting passage of the gas there around into said nozzle passageway;

an electrode fixed at a rear end thereof in said receiving hole of said first support portion to enable said electrode to extend into said nozzle passageway, said electrode capable of receiving electrical energy via a bonding wire to bring about a high voltage discharge;

said nozzle passageway provided therein with a second support portion having at least one channel for passage of the gas, and a passage for said electrode to pass therethrough; and wherein a cross-sectional area through the first support portion and the handle is greater than that through the second support portion and the nozzle.

9. The electrosurgical hand piece as defined in claim 8, wherein said nozzle is provided on an outer surface with a contacting portion for use in moving away a healthy tissue obstructing a diseased or deformed tissue under treatment;

wherein said contacting portion is an annular projection with an outer diameter greater than that of the nozzle, the projection having a rear side spaced apart from a corresponding end of the handle and a front side which is inclined to the outlet of the nozzle.

10. The electrosurgical hand piece as defined in claim 8, further comprising a grip on the handle for gripping the hand piece by a user, the grip being adjustable on the handle.

11. The electrosurgical hand piece as defined in claim 8, wherein said second support portion of said nozzle is engaged to a tubular wall of said nozzle passageway and is radially provided with a plurality of ribs such that said channel is formed between two adjoining ribs, and that said passage is formed between free ends of said ribs.

12. The electrosurgical hand piece as defined in claim 8 wherein said second support portion is formed by a support member provided in said nozzle passageway of said nozzle; said support member being a tubular construction and provided in an interior with a plurality of ribs extending radially such that said channel is formed between two adjoining ribs, and that said passage is formed between free ends of said ribs.

13. The electrosurgical hand piece as defined in claim 8, wherein said nozzle comprises a base and a head engaged to the base, said base being provided at a rear end with said first support portion, and at a front end with a receiving hole, said head being provided with said nozzle passageway, said head being fixed at one end thereof in said receiving hole of said base, said base being fixed in said handle.

14. The electrosurgical hand piece as defined in claim 8, further comprising a contacting portion formed by at least one protruded ring on a front end of said nozzle spaced apart from a corresponding end of the handle.

* * * * *